(12) United States Patent
Osawa et al.

(10) Patent No.: US 7,083,577 B2
(45) Date of Patent: Aug. 1, 2006

(54) GUIDE WIRE

(75) Inventors: Shinji Osawa, Osaka (JP); Hiroyuki Inoue, Osaka (JP); Kazuhiro Fukuchi, Osaka (JP); Masahisa Tanimoto, Osaka (JP)

(73) Assignee: Nipro Corporation, Osaka (JP)

( * ) Notice: Subject to any disclaimer, the term of this patent is extended or adjusted under 35 U.S.C. 154(b) by 475 days.

(21) Appl. No.: 10/279,104

(22) Filed: Oct. 24, 2002

(65) Prior Publication Data

US 2003/0083622 A1    May 1, 2003

(30) Foreign Application Priority Data

Oct. 25, 2001 (JP) ............................. 2001-327415
May 20, 2002 (JP) ............................. 2002-145124

(51) Int. Cl.
*A61B 5/00* (2006.01)
*A61M 25/00* (2006.01)

(52) U.S. Cl. ...................... 600/585; 600/433; 600/434; 600/435; 604/164.13

(58) Field of Classification Search ................ 600/585, 600/433, 434, 435; 604/164.13
See application file for complete search history.

(56) References Cited

U.S. PATENT DOCUMENTS

| | | | |
|---|---|---|---|
| 4,003,369 A | | 1/1977 | Heilman et al. ............ 128/2 M |
| 4,721,117 A | * | 1/1988 | Mar et al. .................... 600/585 |
| 4,846,186 A | | 7/1989 | Box et al. .................... 128/657 |
| 5,095,915 A | * | 3/1992 | Engelson ..................... 600/585 |
| 5,135,503 A | | 8/1992 | Abrams ....................... 604/164 |
| 5,484,409 A | | 1/1996 | Atkinson et al. ............. 604/96 |
| 5,497,783 A | * | 3/1996 | Urick et al. ................. 600/585 |
| 5,743,876 A | * | 4/1998 | Swanson ................. 604/96.01 |
| 6,527,732 B1 | * | 3/2003 | Strauss et al. .............. 600/585 |
| 6,740,050 B1 | * | 5/2004 | D'Aquanni et al. ........ 600/585 |

FOREIGN PATENT DOCUMENTS

| | | |
|---|---|---|
| DE | 44 06 077 A1 | 9/1994 |
| EP | 1 070 512 A1 | 1/2001 |
| JP | 06-054911 A | 3/1994 |
| JP | 06-054912 A | 3/1994 |
| JP | 7-37199 U | 7/1995 |

* cited by examiner

*Primary Examiner*—Max F. Kindenburg
*Assistant Examiner*—Rene Towa
(74) *Attorney, Agent, or Firm*—Kubovcik & Kubovcik (57) ABSTRACT

A guide wire having an elongated core wire provided with a tabular distal end portion, and a coiled wire provided on an outer circumference of the core wire, wherein the distal end portion of the core wire is provided with a cutout section or a rased section so that a diametrical cross-sectional area of the distal end portion of the core wire gradually decreases toward a distal end thereof.

5 Claims, 5 Drawing Sheets

GUIDE WIRE

BACKGROUND OF THE INVENTION

This invention relates to a guide wire used to introduce a catheter to a necessary position in a human body for a remedy or an examination.

A catheter is used in medical treatment such as super selective angiography, percutaneous transluminal angioplasty (PTA), transcatheter arterial embolization (TAE) or percutaneous transluminal coronary angioplasty (PTCA), etc. In order to introduce the catheter into a human body, a guide wire has been heretofore used. The guide wire is a wire for guiding a catheter. The guide wire is mainly used in a percutaneous catheterization (Seldinger method). In this method, after a guide wire is inserted into a blood vessel, a catheter is inserted into a blood vessel with the guide wire used as a shaft. It is very difficult to insert a catheter into an artery because the pressure in an artery is higher than that in a vein. The catheter can be easily inserted into an artery by placing a guide wire in the artery in advance, and inserting a catheter thereinto along the guide wire.

A guide wire is comprised of, for example, an elongated core wire and a coil wire provided on an outer circumference of a distal end portion of the core wire as disclosed in U.S. Pat. No. 4,846,186, Japanese Patent Laid-Open Nos. 54911/1994 and 54912/1994 and Japanese Utility Model Laid-Open No. 37199/1995. The core wire is a core member, which becomes thin toward the distal end thereof and is formed out of a super-elastic material. The super-elastic material needs to have a suitable flexibility to give follow-up characteristics with respect to a blood vessel, i.e., the capability to select a proper blood vessel at a branch point, to the guide wire and a rigidity high enough to transmit a torque and a pushing force generated at a proximal end of the guide wire to a distal end thereof. The coil wire can be reshaped by plastically deforming the same, and is a metal coil excellent in operability and radiolucency. The core wire and the coil wire are combined by melting a part of the distal end portion of the coil wire to form a guide wire. A guide wire formed by combining the core wire and the coil wire can be deformed at a distal end portion thereof and easily passes through a narrowed portion in a blood vessel. Moreover, the guide wire is formed so that a turning movement generated at a proximal end thereof can be smoothly transmitted to a distal end portion thereof.

A guide wire is occasionally bent or plastically deformed by medical personnel in advance to fit the shape of the guide wire to a shape of a portion of a blood vessel into which a guide wire is to be inserted. In such a case, a guide wire has been developed of which the core wire is provided with an additional attachment called a ribbon at the distal end thereof in order to absolutely and easily deform the distal end of the guide wire (Japanese Patent Laid-Open Nos. 292174/1992, 505561/1995 and 99092/1997 and U.S. Pat. Nos. 4,554,929, 4,998,917 and 5,135,503).

All of the guide wires disclosed in the above-mentioned publications are formed so that the distal end portion thereof is more flexible than the proximal end portion in order to improve a follow-up characteristic with respect to a blood vessel. That is, the core wire composing the guide wire becomes thin toward the distal end thereof, and the ribbon provided at the distal end of the core wire consists of a material having an excellent flexibility or has a smaller cross-sectional area than that of the distal end of the core wire. However, as described above, the core wire needs to provide not only flexibility to the distal end portion of the guide wire but also rigidity high enough to transmit a torque and a pushing force generated at a proximal end of the guide wire to the distal end thereof. Therefore, there is a limit to the extent of reduction of the diameter of the distal end portion of the core wire.

The core wires disclosed in the above-mentioned publications are formed so that the distal end portion of each core wire has a columnar or tabular shape having a constant diameter or width, the rigidity of the distal end portion being thereby maintained. However, since a portion having a constant width in the distal end portion of the core wire has a constant degree of flexibility, i.e. hardness, the rigidity of the distal end portion of the guide wire becomes high. Therefore, there is a fear that the distal end of the guide wire will puncture a blood vessel due to a pushing force transmitted from the proximal end of the guide wire. When a material of the distal end portion of the core wire is changed to a material capable of giving flexibility to the guide wire, it is difficult for torque generated at the proximal end of the guide wire to be transmitted to the distal end thereof.

SUMMARY OF THE INVENTION

The present invention has been made in view of the above-mentioned circumstances, and provides a guide wire having a balanced rigidity and flexibility. This guide wire can be deformed at a distal end portion thereof, easily pass through a narrowed portion in a blood vessel, and can transmit a torque and a pushing force generated at a proximal end of the guide wire to a distal end thereof. Using the guide wire of the present invention, there is no fear that the distal end of the guide wire will puncture a blood vessel.

In order to solve the above-mentioned problem, the inventors of the present invention discovered that, when a core wire is formed so that the flexibility of a distal end portion of the core wire gradually increases toward a distal end thereof by providing a cutout section or a rased section in a tabular shaped portion, which has a constant width and is provided at a distal end of the core wire, a guide wire free from the above-mentioned drawbacks can be provided, and reached the present invention.

Namely, the present invention relates to a guide wire having an elongated core wire provided with a tabular distal end portion, and a coil wire provided on an outer circumference of the core wire, wherein the distal end portion of the core wire is provided with a cutout section or a rased section so that a diametrical cross-sectional area of the distal end portion gradually decreases toward a distal end thereof. The tabular distal end portion of the core wire may be a part of the core wire or be composed of an attachment different from the core wire.

DESCRIPTION OF THE DRAWINGS

The guide wire according to the present invention will now be described in detail on the basis of preferred embodiments shown in the attached drawings. However, the present invention is not limited to these embodiments.

FIGS. 3-A–3-C are enlarged views showing an example of a distal end portion of a core wire constituting a guide wire, wherein the distal end portion has a cutout section.

FIGS. 4-A–4-C are enlarged views showing an example of a distal end portion of a core wire constituting a guide wire, wherein the distal end portion has two rased sections.

FIGS. 5-A–5-C are enlarged views showing an example of a distal end portion of a core wire constituting a guide wire, wherein the distal end portion has four rased sections.

FIGS. 6-A–6-C are enlarged views showing another example of a distal end portion of a core wire constituting a guide wire, wherein the distal end portion has a cross-sectional area which phases down and has a cutout section.

FIGS. 7-A–7-C are enlarged views showing another example of a distal end portion of a core wire constituting a guide wire, wherein the distal end portion has a cross-sectional area which phases down and has two rased sections.

FIGS. 8-A–8-C are enlarged views showing another example of a distal end portion of a core wire constituting a guide wire, wherein the distal end portion has a cross-sectional area which phases down and has four rased sections.

FIGS. 9-A–9-C are enlarged views showing another example of a distal end portion of a core wire constituting a guide wire, wherein the distal end portion is a combination of tabular members and has four rased sections.

DETAILED DESCRIPTION OF THE INVENTION

Figure 1:
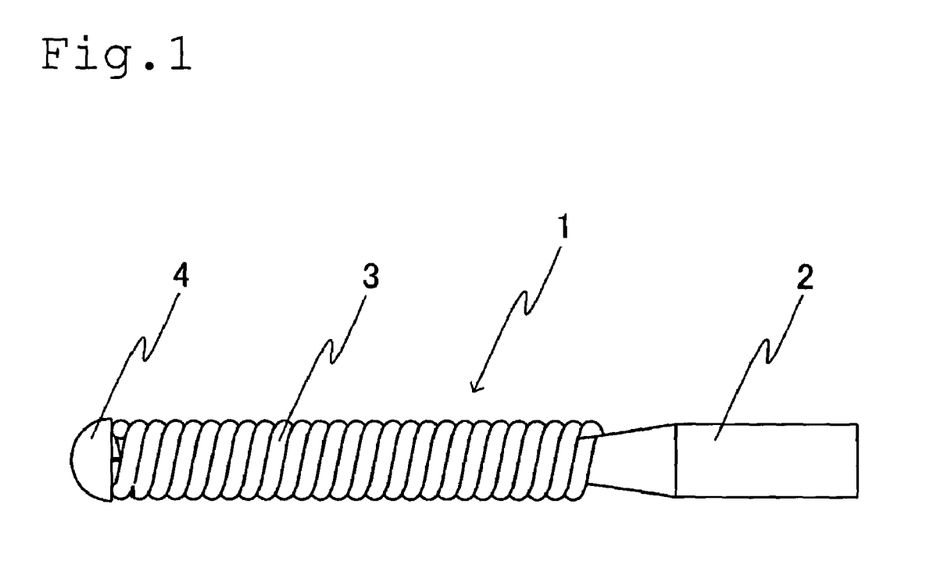
FIG. 1 is a side view of a distal end of a guide wire according to the present invention.
Figure 2:
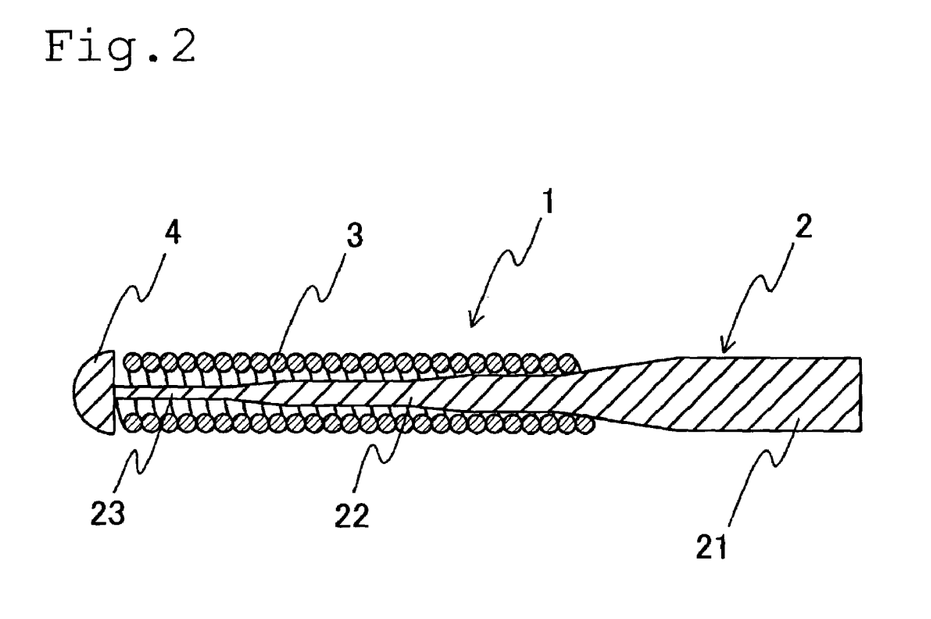
FIG. 2 is a longitudinal sectional view showing an example of a guide wire having a core wire of which a distal end portion is a part of the core wire.
Figure 10:
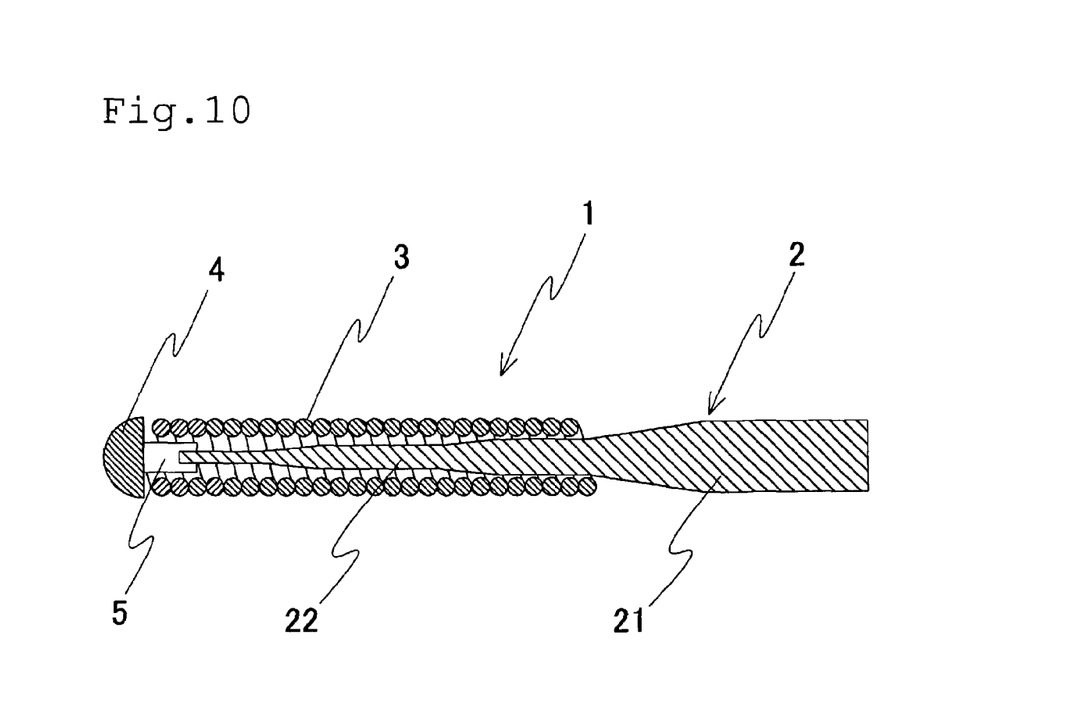
FIG. 10 is a longitudinal sectional view showing an example of a guide wire having a core wire of which a distal end portion is an attachment different from the core wire.

In the guide wire according to the present invention, a distal end indicates an end at which a patient is pierced (left side in FIGS. 1, 2 and 10), while a proximal end indicates an end which is held by medical personnel when the guide wire is operated, and which is at the opposite end of the distal end (right side in FIGS. 1, 2 and 10). An axial direction indicates a direction connecting the above-mentioned distal end and proximal end together, and a diametrical direction indicates a direction perpendicular to the axial direction.

As shown in FIG. 1, a guide wire 1 according to the present invention includes an elongated core wire 2, and a coil wire 3 provided on an outer circumference of a distal end of the core wire 2.

As shown in FIG. 2, the core wire 2 is preferably an elongated wire having a substantially circular diametrical cross section except at the distal end portion thereof. The core wire 2 includes, for example, a main portion 21 on the proximal end side thereof which is held by medical personnel when the guide wire 1 is operated, a tabular distal end portion 23, which has a tabular shape and is formed so that a diametrical cross-sectional area of this portion is smaller than that of the main portion 21, and a transitional portion 22 between the main portion 21 and the distal end portion 23.

The main portion 21 of the core wire 2 in the present invention is preferably an elongated wire having a total length of 175 to 300 cm and a uniform outer diameter of 0.010 to 0.018 inch (0.25 to 0.45 mm). The suitable size of this portion is different depending upon the use of the guide wire. A diametrical cross section of the main portion 21 preferably has a circular shape and the like which decreases resistance when this portion is inserted into a blood vessel. Since the main portion 21 has a uniform outer diameter, this portion has substantially the same flexibility in the axial direction. The main portion 21 also has the largest diametrical cross-sectional area among the portions of the core wire 2, so that a torque and a pushing force which medical personnel apply to the proximal end portion of the guide wire 1 can be transmitted maximally to the distal end portion 23 of the guide wire 1.

Figure 3:
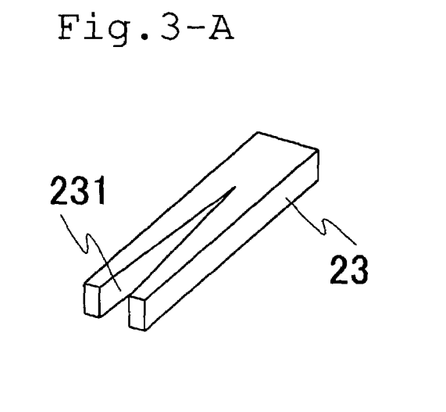

FIGS. 3 to 9 are drawings showing examples of a shape of the distal end portion 23 of the core wire 2 in the present invention. FIGS. 3-A, 4-A, 5-A, 6-A, 7-A, 8-A and 9-A are enlarged perspective views showing various examples of the distal end portion 23. FIGS. 3-B, 4-B, 5-B, 6-B, 7-B, 8-B and 9-B are enlarged side views of these examples of the distal end portion 23 taken in the lateral direction. FIGS. 3-C, 4-C, 5-C, 6-C, 7-C, 8-C and 9-C are enlarged side views of the same examples of the distal end portion 23 taken from the upper side thereof.

Figure 4:
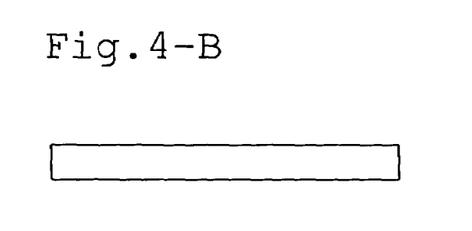
Figure 5:
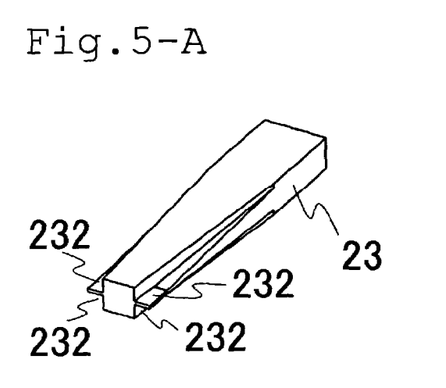

As shown in FIGS. 3 to 5, the distal end portion 23 of the core wire 2 of the guide wire 1 of the present invention preferably has a tabular shape of 5 to 50 mm in axial length, 0.02 to 0.2 mm in length of each side of a diametrical cross-section, and 0.002 to 0.02 $mm^2$ in diametrical cross-sectional area. When the axial length of the distal end portion 23 is smaller than 5 mm, it becomes difficult to form a cutout section or a rased section in the distal end portion, and the rigidity thereof becomes too high. When this length is larger than 50 mm, a torque generated at the proximal end of the guide wire 1 becomes difficult to be transmitted to the distal end thereof.

Figure 6:
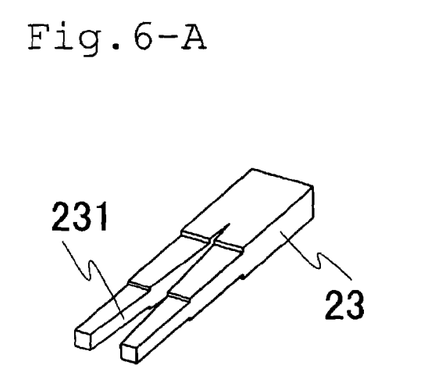
Figure 7:
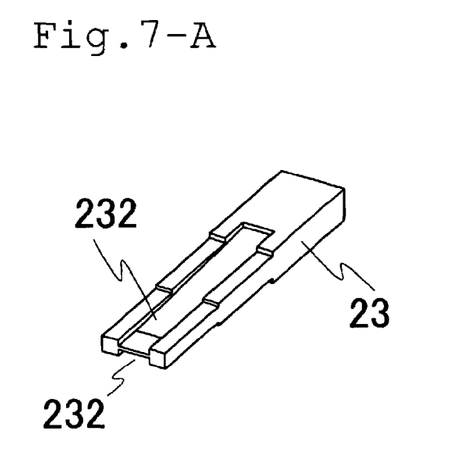
Figure 8:
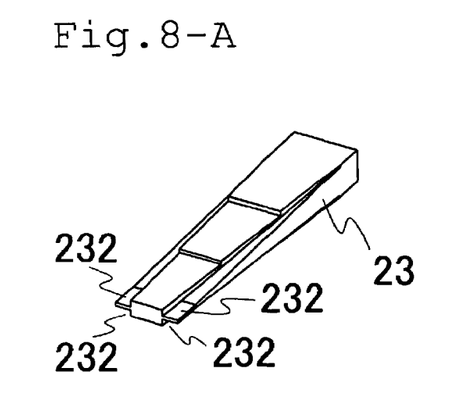
Figure 9:
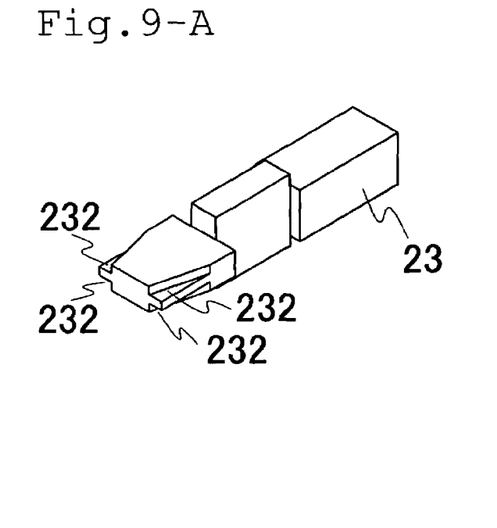

The distal end portion 23 may have a tabular shape of which the diametrical cross-sectional area gradually decreases toward the distal end as shown in FIGS. 6 to 8. In this case, the number of phases in which the diametrical cross-sectional area phases down is not particularly limited. However, when the number of the phases is too large, the molding of the distal end portion becomes difficult, and, therefore, the number of phases is preferably not larger than 3. As shown in FIG. 9, the distal end portion 23 may be formed of a combination of tabular members the diametrical cross-sectional areas of which phase down by reducing the diametrical length of one side and increasing that of the other. The diametrical cross-sectional areas of distal end portion 23 shown in FIG. 9 also preferably phase down in three phases as well as that of the distal end portion 23 shown in FIGS. 6 to 8. When the distal end portion 23 has a shape the diametrical cross-sectional area of which phases down as shown in FIGS. 6 to 9, the cross-sectional area of the foremost end of the distal end portion is preferably larger than 0.002 $mm^2$ taking torque transmission characteristics thereof into consideration.

The distal end portion 23 of the core wire 2 in the present invention is provided with a cutout section or a rased section so that the diametrical cross-sectional area of the distal end portion gradually decreases toward the distal end thereof. Since the guide wire 1 according to the present invention is provided with a cutout section or a rased section at the tabular distal end portion 23 of the core wire 2, the flexibility of the distal end portion of the guide wire 1 becomes gradually higher toward the distal end thereof. Therefore, the guide wire 1 has a flexibility suitable for the insertion thereof into a blood vessel and there is no fear that the guide wire will puncture a blood vessel because the distal end thereof is too hard or that torque generated at the proximal end of the guide wire becomes difficult to be transmitted to the distal end thereof because the distal end thereof is too soft, which are the problems of a conventional guide wire provided with a distal end portion having a constant flexibility.

The distal end portion 23 of the core wire 2 shown in FIG. 3 has a tabular shape as shown in FIG. 3-B. The distal end portion 23 is provided with a cutout section 231 extending from a distal end of the distal end portion 23 toward a proximal end thereof and passing through from one side surface to the opposite side surface thereof as shown in FIG. 3-C. The cutout section 231 is preferably formed by cutting out of the distal end portion 23 a triangular shape having a base at a distal end thereof and an apex at a proximal end thereof. The cutout section 231 may also have any other shape as long as the cutout section is formed by cutting out of the distal end portion 23 a shape which gradually enlarges toward the distal end thereof.

It is preferable that the cutout section 231 be formed so as to extend from the distal end toward the proximal end by a distance corresponding to 10 to 70% of the axial length of the distal end portion 23. When the axial length of the cutout section 231 is smaller than the range mentioned above, there is no effect that the distal end portion 23 has gradual increase in flexibility toward the distal end thereof. When the axial length of the cutout section 231 is larger than the above-mentioned range, the rigidity of the distal end portion 23 becomes insufficient.

It is preferable that the diametrical cross-sectional area of the foremost end of the distal end portion 23 having the cutout section 231 be not smaller than 50% of that of the rearmost proximal end of the distal end portion 23. When the diametrical cross-sectional area of the foremost end of the distal end portion 23 becomes smaller than the above-mentioned range, the rigidity of the distal end portion 23 becomes insufficient, and a torque and a pushing force generated at the proximal end of the guide wire 1 becomes difficult to be transmitted to the distal end thereof.

Since the cutout section 231 is provided in this manner, the distal end portion 23 of the core wire 2 has a diametrical cross-sectional area that gradually decreases toward the distal end, so that the flexibility of the guide wire 1 gradually increases toward the distal end. Therefore, the inserting of the guide wire 1 into a blood vessel can be done more safely and easily.

A distal end portion 23 of the core wire shown in FIG. 4 has a tabular shape as shown in FIG. 4-B. As shown in FIG. 4-C, a rased section 232 is provided at the center of each of two opposed side surfaces of the distal end portion 23 so that the thickness of the distal end portion 23 becomes smaller from a proximal end thereof toward a distal end thereof. One rased section 232 can be provided in one of the side surfaces of the distal end portion 23 but the direction in which the distal end of the guide wire 1 is liable to be bent is limited. Therefore, it is preferable that two rased sections 232 are provided symmetrically with respect to the longitudinal axis of the distal end portion 23 as shown in FIG. 4-C. Since the distal end portion 23 has a tabular shape, it is more preferable that the rased sections 232 are provided in the larger side surface since this enables a molding operation to be easily carried out.

The distal end portions 23 having rased sections 232 include a distal end portion 23 shown in FIG. 5 as another example. The distal end portion 23 shown in FIG. 5 is provided with two rased sections 232 at the outer edge portions of each of two opposed side surfaces thereof so that the thickness of the distal end portion 23 becomes smaller from a proximal end thereof toward a distal end thereof.

The rased sections 232 are preferably formed so as to extend from the distal end of the distal end portion 23 toward the proximal end thereof by a distance corresponding to 10 to 70% of the axial length of the distal end portion 23 the same as the cutout sections 231 shown in FIG. 3. It is also preferable that the rased sections 232 be formed so that the diametrical cross-sectional area of the foremost end of the distal end portion 23 is not smaller than 50% of that of the rearmost proximal end thereof.

The rased sections 232 thus formed can give the same effect to the guide wire 1 as the above-mentioned cutout sections 231.

FIGS. 6 to 9 show other concrete examples of the shape of the distal end portion 23 of the core wire 2 constituting the guide wire 1 according to the present invention.

A distal end portion 23 of a core wire 2 shown in FIG. 6 has a tabular shape of which the diametrical cross-sectional area phases down toward the distal end as shown in FIG. 6-B. The distal end portion 23 is provided with a cutout section 231 extending from a proximal end of the distal end portion 23 toward the distal end thereof and passing through from one side surface to the opposite side surface thereof as shown in FIG. 6-C. The shape of the cutout section 231 is identical with that of the cutout section 231 as shown in FIG. 3.

A distal end portion 23 of a core wire 2 shown in FIG. 7 has a tabular shape of which a cross-sectional area phases down toward the distal end thereof as shown in FIG. 7-B. The distal end portion 23 is provided with a rased section 232 at each of two opposed side surfaces thereof the same as the distal end portion of the core wire 2 shown in FIG. 4. In such a manner, the thickness of the distal end portion 23 becomes smaller from a proximal end thereof to the distal end thereof.

A distal end portion 23 of a core wire 2 shown in FIG. 8 has a tabular shape of which the cross-sectional area phases down toward the distal end thereof as shown in FIG. 8-B. The distal end portion 23 is provided with two rased sections 232 at the outer edge portions of each of two opposed side surfaces of the distal end portion 23 so that the thickness of the distal end portion 23 decreases from a proximal end thereof toward the distal end thereof the same as the distal end portion 23 of the core wire 2 shown in FIG. 5. The shapes of rased sections 232 of core wires 2 shown in FIGS. 7 and 8 are identical with those of the rased portions 232 shown in FIGS. 4 and 5.

A distal end portion 23 of a core wire 2 shown in FIG. 9 is formed of a combination of tabular members the diametrical cross-sectional area of each of which is phased down by reducing the length of one side of the diametrical cross-sectional area, and increasing that of the other as shown in FIG. 9-A. The distal end of the distal end portion 23 is provided the same as the core wires 2 shown in FIGS. 5 and 8 with two rased sections 232 at the outer edge portions of each of two opposed side surfaces thereof so that the thickness becomes smaller from a proximal end toward a distal end thereof. Instead of these rased sections 232, a cutout section 231 as shown in FIGS. 3 and 6, and rased sections 232 as shown in FIGS. 4 and 7 may be provided, though illustrations are not included.

The core wires 2 shown in FIGS. 6, 7, 8 and 9 have a tabular shape the cross-sectional area of which phases down toward the distal end thereof as compared with the core wires 2 shown in FIGS. 3, 4 and 5. This enables the distal end portion 23 to be made specially flexible, and enables a fine plastic deformation of the distal end of the guide wire 1. The shapes of these core wires 2 can be determined selectively in accordance with the use of the guide wire 1.

The transitional portion 22 of the core wire 2 in the present invention is a portion connecting the main portion 21 and distal end portion 23. The transitional portion 22 preferably decreases in its diameter from the proximal end thereof toward the distal end thereof. The transitional portion 22 is preferably 20 to 50 cm in axial length, and circular in diametrical cross-section. The transitional portion 22 may have the form of any structure including a tapered structure the diameter of which decreases at a predetermined rate, a structure the diameter of which phases down, or a structure of a combination of a tapered portion and a portion the diameter of which phases down, as long as the structure continuously or gradually varies the rigidity and elasticity of the main portion 21 and the distal end portion 23. More preferably, the transitional portion 22 has three tapered sections so as to phase down in three phases. Owing to the provision of this transitional portion 22, stress is not locally concentrated on the guide wire 1, and the occurrence of a kink in the guide wire 1 can be prevented.

The core wire 2 in the present invention is preferably formed of a highly elastic material having both a rigidity high enough to transmit a torque and a pushing force generated at the proximal end of the guide wire 1 toward the distal end thereof, and a flexibility high enough to eliminate a fear that the distal end of the guide wire 1 will puncture a blood vessel. The highly elastic materials include stainless steel, tungsten, tantalum, an alloy containing these materials as main components and an amorphous alloy and the like. In the core wire 2 in the present invention, all of the main portion 21, the transitional portion 22 and the distal end portion 23 may be formed out of the same material, or some of them may be formed out of different materials.

The main portion 21, the transitional portion 22 and distal end portion 23 of the core wire 2 are preferably formed by a press molding using a pressing machine.

The distal end portion 23 of the core wire 2 may be composed of an attachment referred to as a ribbon which is different from the core wire 2 as shown in FIG. 10. When medical personnel bend or plastically deform the guide wire 1 in advance to fit the shape of the guide wire 1 to a shape of a portion into which the guide wire 1 is inserted, the guide wire 1 having the ribbon 5 is absolutely and easily deformed at the distal end of the guide wire 1. The shape of the ribbon 5 is the same shape as the distal end portions 23 of the core wires 2 as shown in FIGS. 3 to 9.

The ribbon 5 is comprised of a super-elastic material such as stainless steel, tungsten, tantalum, an alloy containing these materials as main components or an amorphous alloy and the like. The ribbon 5 is formed by, for example, a press molding or a converting using a laser after forming by a press molding. The ribbon 5 is preferably connected to the distal end of the core wire 2 by means of welding, brazing or the like.

The coil wire 3 in the present invention is provided on an outer circumference of the distal end portion of the core wire 2. The coil wire 3 is preferably obtained by coiling a wire of 0.04 to 0.10 mm in outer diameter so as to form a coil wire of 200 to 500 mm in axial length and 0.2 to 0.45 mm in outer diameter. The coil wire 3 is provided on the core wire 2 by winding the coil wire 3 on the core wire 2, or inserting the core wire 2 into an inner portion of the coil wire helically wound in advance. Both ends of the coil wire 3 are fixed on the core wire 2 by bonding using an adhesive, soldering, brazing or the like. The fixing method using brazing is preferable because it does not give a fear that the core wire 2 and coil wire 3 will separate from each other while they are inserted into a blood vessel. Furthermore, it is preferable that the distal end of the core wire 2 and that of the coil wire 3 are connected by melting the distal end portion of the coil wire 3 and forming a hemispherical distal end tip 4 shown in FIGS. 1, 2 and 10.

The coil wire 3 is formed mostly out of a radiation permeable material, such as stainless steel, an amorphous alloy and the like. However, the guide wire 1 is used to confirm the position of a distal end thereof in a blood vessel by applying X-rays thereto when the guide wire 1 is inserted into the blood vessel. Therefore, it is preferable that at least the distal end portion of the coil wire 3 is formed out of a material having a radiolucency. Materials having excellent radiolucency include known radiopaque materials, such as platinum, gold, iridium, tungsten, tantalum, etc., among which platinum is preferably used. A coil wire formed by axially winding a plurality of wires of different materials as disclosed in the specification of the already-filed Japanese Patent Application No. 111118/2001 may also be used as the coil wire 3.

The coil wire 3 may be formed by subjecting a cast wire to cold working.

The guide wire 1 according to the present invention is formed by providing the coil wire 3 on the outer circumference of the distal end portion of the core wire 2. The distal end portion of the coil wire 3 can be plastically deformed, and medical personnel can bend the distal end portion of the guide wire having the coil wire 3 to fit the shape thereof to a shape of a portion of a blood vessel into which the guide wire is to be introduced. The core wire 2 and the ribbon 5 are made of a highly elastic material and not plastically deformed. However, the core wire 2 and the ribbon 5 can be deformed in accordance with the shape of the coil wire 3. The guide wire 1 having the ribbon 5 can be finely deformed because of the flexibility of the distal end portion of the ribbon 5.

The guide wire 1 according to the present invention may be covered at a necessary portion thereof with a synthetic resin, such as polyurethane and nylon on the circumference of the core wire 2 and coil wire 3 according to the intended use of the guide wire 1. This enables the flexibility of the distal end of the guide wire 1 to be improved, the outer surface of the guide wire to become smooth, and a fear of damaging the inner surface of a blood vessel to be further decreased. The guide wire 1 may also be coated with a hydrophilic lubricant, such as maleic acid anhydride, polyvinyl pyrrolidone, etc., an anticoagulant, an antithrombus material or the like.

The guide wire according to the present invention is inserted into a blood vessel of a human by three actions including a turning action, a pushing action and a pulling action by medical personnel. A catheter is thereafter slid on the guide wire and inserted into the interior of the blood vessel. When it is ascertained that the guide wire does not advance in the interior of the blood vessel, the guide wire is withdrawn from the blood vessel with the catheter alone left therein. After extension of the blood vessel is ascertained with a contrast medium injected into the blood vessel through the interior of the catheter, the guide wire is inserted again. When the catheter is advanced to a final object position, the guide wire is withdrawn from the blood vessel, a contrast medium is injected into the blood vessel through the catheter to ascertain the object portion of the blood vessel, or an embolus is injected into the catheter to kill a tumor. When a balloon catheter is used instead of the catheter, a chorkbore in a blood vessel can be opened or expanded by placing the balloon or a stent at the chorkbore in the blood vessel.

Effect of the Invention

Since the guide wire according to the present invention is formed of a core wire, a coil wire and a ribbon as occasion demands, the guide wire is excellent in the variability, i.e., the property of being plastically deformed, of the distal end portion thereof and the capability of the same portion of being inserted into the interior of a blood vessel both of which are necessary for the guide wire. Since the diametrical cross-sectional area of the distal end portion of the core wire is gradually reduced toward the distal end side due to a cutout section or a rased section, the flexibility of the distal end portion of the guide wire is improved and, at the same time, the rigidity thereof can also be maintained. This enables elimination of a fear that the distal end portion of the guide wire will,damage or puncture a blood vessel, and enables a torque and a pushing force generated at the proximal end of the guide wire to be transmitted to the distal end thereof, and a guide wire superior in operability to a conventional guide wire to be provided. Additionally, the guide wire having the ribbon can be finely deformed at the distal end of the guide wire and operability of the guide wire during insertion into the blood vessel is improved.

What is claimed is:

1. A guide wire comprising an elongated core wire having a distal end and a proximal end, and a coil wire provided on an outer circumference of the distal end of the core wire, said distal end comprising a tabular shaped section at a distal most end thereof, characterized in that said tabular shaped section is provided with a cutout section extending in an axial direction of the core wire so that a diametrical cross-sectional area of said tabular shaped section gradually decreases toward the distal most end of the core wire, said cutout section being formed by cutting out of said tabular shaped section a triangular shape having a base at a distal end of the cutout section and an apex at a proximal end of the cutout section.

2. The guide wire according to claim 1, wherein said tabular shaped section is further provided with at least two rased sections which are symmetrical with respect to a longitudinal axis of said tabular shaped section.

3. The guide wire according to claim 1, wherein said cutout section is formed so as to extend axially 10 to 70% the length of said tabular shaped section from said distal end toward the proximal end.

4. The guide wire according to claim 1, wherein the diametrical cross-sectional area of said tabular shaped section phases down toward said distal end thereof.

5. The guide wire according to claim 1, wherein said tabular shaped section of the core wire is composed of a material different from that of the core wire.

\* \* \* \* \*